United States Patent [19]
Schleifer et al.

[11] Patent Number: 6,077,674
[45] Date of Patent: Jun. 20, 2000

[54] METHOD OF PRODUCING OLIGONUCLEOTIDE ARRAYS WITH FEATURES OF HIGH PURITY

[75] Inventors: Arthur Schleifer, Portola Valley; May Tom-Moy, San Carlos, both of Calif.

[73] Assignee: Agilent Technologies Inc., Palo Alto, Calif.

[21] Appl. No.: 09/428,332

[22] Filed: Oct. 27, 1999

[51] Int. Cl.$^7$ .............................. C12Q 1/68; C12P 19/34; C07H 21/04; C07H 21/00
[52] U.S. Cl. ................... 435/6; 435/6; 435/91.2; 536/24.3; 536/25.3
[58] Field of Search ..................... 435/6, 91.2; 536/24.3, 536/25.3

[56] References Cited

U.S. PATENT DOCUMENTS 5,837,860  11/1998  Anderson et al. ...................... 536/25.3
5,858,653   1/1999  Duran et al. ................................. 435/6

FOREIGN PATENT DOCUMENTS

WO 98/18961  5/1998  WIPO .
WO 98/39481  9/1998  WIPO .

OTHER PUBLICATIONS

Jerzy Olejnik, et al, "Photocleavable aminotag phosphoramidites for 5'–termini DNA/RNA labeling," *Nucleic Acids Research*, vol. 26, No. 15, 1998, pp. 3572–3576.

Alan F. Cook, et al, "Synthesis and hybridization of a series of biotinylated oligonucleotides," *Nucleic Acids Research*, vol. 16, No. 9, 1988, pp. 4077–4095.

Jerzy Olejnik, et al, "Photocleavable biotin phosphoramidite for 5'–end–labeling, affinity purification and phosphorylation of synthetic oligonucleotides," *Nucleic Acid Research*, vol. 24, No. 2, 1996, pp. 361–366.

Rainer Bischoff, et al, "Introduction of 5'–terminal functional groups into synthetic oligonucleotides for selective immobilization," *Analytical Biochemistry*, vol. 164, 1987, pp. 336–344.

*Primary Examiner*—Michael P. Woodward
*Assistant Examiner*—Jeffrey S. Lundgren
*Attorney, Agent, or Firm*—Elizabeth E. Leitereg; Gordon Stewart

[57] ABSTRACT

A method of making full-length oligonucleotide arrays provides for the purification of pre-synthesized full-length oligonucleotides from shorter length oligonucleotides and other impurities at the same time the oligonucleotides are deposited on the array. A synthesized mixture that includes desired full-length oligonucleotides and some capped shorter length or "failed" oligonucleotide sequences, is reacted with a linking agent to add a linking group on to the free-end of the full-length oligonucleotides but not the shorter-length oligonucleotides. The resulting mixture is deposited on an array without first separately purifying the mixture to remove the unwanted shorter-length oligonucleotides. After deposition, unbound material, including the shorter length oligonucleotide sequences and other impurities, is removed.

42 Claims, 3 Drawing Sheets

METHOD OF PRODUCING OLIGONUCLEOTIDE ARRAYS WITH FEATURES OF HIGH PURITY

TECHNICAL FIELD

This invention relates to a tools and methods used for monitoring levels of gene expression and mutations in gene sequences. In particular, the invention relates to a method of making oligonucleotide arrays, which combines the purification and assembly of full-length oligonucleotides onto an array into one step.

BACKGROUND ART

There are two basic methods for creating oligonucleotide arrays. One technique is to synthesize the oligonucleotide array in discrete feature locations on the array, nucleotide by nucleotide, using well-known phosphoramidite synthesis chemistry. This method is called in situ oligonucleotide array synthesis. The phosphoramidites used for in situ synthesis may be spotted on the array using inkjet deposition equipment manufactured by Hewlett-Packard of California, for example, to create a spatially unique pattern of oligonucleotides. Four inkjet nozzles are used to place the different phosphoramidites onto the array substrate. The array of features on the substrate may be physically separate or there may be no space between such features. In situ synthesis involves the repetitive steps of deblocking, coupling, capping and oxidizing, which are well known in the art, until the desired full-length oligonucleotides are synthesized.

While in situ synthesis is a very flexible means for producing DNA arrays, the fidelity or percentage of full-length oligonucleotides synthesized within a feature on the array is less than 100 percent. An ideal array will have only full-length oligonucleotides attached to each feature. The ideal array promotes accuracy in hybridization experiments or assays of target biological materials. If the fidelity of an in situ generated array is less than 100 percent, it typically has non full-length oligonucleotides within a feature that usually consists of shorter lengths of the correct sequence and to a lesser degree, incorrect sequences. Typical DNA coupling efficiencies are around 97 to 99 percent for the standard phosphoramidite chemistry. For oligonucleotides that are 25 nucleotides in length, these efficiencies result in only 46 to 77 percent full-length oligonucleotides contained within a feature ($0.97^{25}$ to $0.99^{25}$). This loss of fidelity can cause chemical noise in hybridization experiments and/or difficulty in developing hybridization conditions. The loss of fidelity can also lead to difficulty in interpreting the data.

Photolithography is a method used by Affymetrix in California to produce in situ arrays using procedures that are similar to those used in the semi-conductor industry. In procedure described by Fodor et al. from Affymetrix U.S. Pat. No. 5,405,783, a photo-deprotection step is used where the protecting group on the phosphoramidite is removed by exposing a photosensitive protecting group to light. Four photo masks are used to create patterns to de-protect areas of the substrate and then a nucleotide is added to these regions. This technique requires four masks for each layer of nucleotides. While this technique allows for production of high-density oligonucleotide arrays, it is less efficient than traditional phosphoramidite synthesis chemistry. With efficiencies of about 90 to 95 percent, the percentage of full-length oligonucleotides within a feature is further reduced to about 9 to 27 percent for oligonucleotides that are 25 nucleotides long ($0.90^{25}$ and $0.95^{25}$).

Deposition or spotting of pre-synthesized oligonucleotides is another method of creating DNA arrays. The process usually consists of synthesizing the oligonucleotides on a commercial DNA synthesizer, wherein a nucleotide is attached to a solid support at its 3' end and the oligonucleotide is built upon its 5' end using the well known repetitive steps of detritylation, coupling, capping, and oxidation. When the synthesis is complete, a final deprotection and cleavage step is performed to release the 3' end of the first nucleotide from the support for attachment to the array substrate. Before the synthesized oligonucleotide is attached to an array substrate, a purification step is required because the synthesis results in a mixture of full-length product and a percentage of incorrect shorter length oligonucleotides. Without a purification step, the feature fidelity would be similar to the in situ synthesized oligonucleotide arrays, described above.

The purification step can be performed in a number of well-known conventional ways. One method is to use a solid phase column to perform the separation of the full-length sequences from the incorrect shorter length sequences by keeping the trityl-protecting group (DMT) on the last nucleotide in the sequence. This is called "trityl on" synthesis. Only the full-length oligonucleotide sequences should have the trityl group still attached, because shorter length chains have been capped off in the capping step. The solid phase purification column has a high affinity for the trityl group and retains it on the column while allowing the incomplete sequences without the trityl group to pass through. Cleavage of the trityl group from the full-length oligonucleotides is accomplished by applying an acidic solution to the column. Finally, the full-length oligonucleotides are eluted from the column with an acetonitrile and water solution. The eluting solution will contain primarily only full-length product. Another well-known purification method uses liquid chromatography (LC). The synthesized oligonucleotide solution is run on a LC system where the full-length oligonucleotides are separated from the incorrect and short sequences and the fraction containing only the full-length oligonucleotide solution is collected. These purification steps are expensive, time consuming, prone to loss of product, and dilution of the final concentration of the oligonucleotide solution.

At the 3' end attachment to the solid support, typically a linker can be used that contains an amino group, for example. After the oligonucleotide is cleaved from the solid support, the 3'-amino group is available to attach the oligonucleotide to the array substrate. In this conventional procedure, any oligonucleotide synthesized, including the shorter-length or incorrect sequences, will have its 3'-amino group available for attaching to the array surface. Except for the conventional purification step, there is nothing preventing the shorter-length or incorrect sequences from attaching to the array surface during the deposition step. Without a purification step, there is a lower than desired percentage of full-length oligonucleotides in the feature. Thus, to achieve a high-fidelity oligonucleotide feature using the conventional methods, one must purify the solution prior to deposition.

There are two well-known basic techniques for spotting pre-synthesized oligonucleotides onto an array. Pin spotting is one technique where metal pins are dipped into solutions of pre-synthesized oligonucleotides and then touched onto a substrate. A small amount of the solution is transferred to the substrate surface. The other technique uses the inkjet equipment, mentioned above, to spot the solutions of pre-synthesized oligonucleotides. The inkjets are loaded with the pre-synthesized oligonucleotide solutions. The inkjets deposit the oligonucleotides onto the surface in a computer-controlled fashion. Arrays of cDNA are also fabricated using the spotting techniques.

The pre-synthesized oligonucleotides may be linked or attached to the array substrate surface by well-known conventional methods. One method includes the covalent linkage of a chemically modified oligonucleotide (e.g. aliphatic 1° amine) to the substrate surface bearing an amine-reactive group (e.g. aromatic isothiocyanate). Another method includes adsorption to a substrate surface coated with a positively charged polyelectrolyte (e.g. poly-L-lysine), followed by cross-linking to the surface chemically or photochemically (e.g. covalent stabilization via ultraviolet (UV) photo-crosslinking).

Olejnik, J. et al., "Photocleavable biotin phosphoramidite for 5'-end-labeling, affinity purification and phosphorylation of synthetic oligonucleotides", *Nucleic Acids Research*, 1996, Vol. 24, No. 2, pp. 361–366, describes the synthesis of a photocleavable biotin phosphoramidite (PCB) for attaching to the 5'-end of a synthetic oligonucleotide. The 5'-PCB end of the oligonucleotide binds to streptavidin for streptavidin affinity purification of the oligonucleotide from failure sequences. The PCB is photocleaved after purification. The affinity purification method disclosed by Olejnik et al. is a complex method that includes adding the crude 5'-PCB oligonucleotide to a suspension of streptavidin-agarose beads which are then incubated, spin-filtered, washed and spin-filtered multiple times again, resuspended, irradiated, spin-filtered and washed again.

Thus, it would be advantageous to have a method of making an array of oligonucleotides that comprises essentially only full length oligonucleotides, which did not require the laborious purification steps, and at the same time, would yield a purity of greater than 90% full length oligonucleotides on the array. The arrays so produced could provide higher quality assay results. Such a method would solve a long-standing problem in the art of making arrays.

SUMMARY OF THE INVENTION

The present invention provides a method of making oligonucleotide arrays with a high percentage of full-length oligonucleotides that combines a purification step or "an enrichment of full length oligonucleotide attachment" with the deposition step. The method uses the well-known synthesis chemistries to pre-synthesize oligonucleotides on a support, and preferably the phosphite-triester synthesis chemistry is used. Moreover, conventional supports are used in the invention, which are defined below. However, after the last nucleotide is added to the oligonucleotide sequence, the present method includes the step of reacting a linking agent to the free-end of the full-length oligonucleotides. The shorter-length oligonucleotides are capped during a conventional capping step and therefore do not couple with the linking agent. The linking agent on the full-length oligonucleotides provides a means for the full-length oligonucleotides to preferentially attach to an array substrate over any other oligonucleotides present, such as the shorter-length oligonucleotides.

In a preferred embodiment, the linking agent is an amine-providing agent, which adds s an amino group to the full-length oligonucleotides. All of the shorter length sequences have been capped in the conventional capping step. Therefore, the amino group is not added to the shorter-length oligonucleotides. During the conventional cleaving and deprotecting step, a mixture of the full-length oligonucleotides and any other shorter-length oligonucleotides is separated from the support and the amino group on the full-length oligonucleotides is converted to a primary amine. In the preferred embodiment, the support used is standard CPG without an amine linker, so that an amine group is not provided to the oligonucleotide upon cleavage from the support.

In accordance with the method of the invention, advantageously the conventional purification step, which separates the full-length oligonucleotides from the shorter-length oligonucleotides is deleted. Instead the present method comprises depositing the mixture of the cleaved oligonucleotides onto the array. The mixture of cleaved oligonucleotides are simultaneously purified to separate full-length from shorter length oligonucleotides during the step of depositing by the preferential attachment of the inherently more reactive linking group, such as preferably the more reactive primary amine group, present only on the full-length oligonucleotides to the surface of the array. The primary amine on the free-end of the full-length oligonucleotide preferentially attaches to the substrate over secondary amines (contained within the structure of the oligonucleotide), because primary amines are more chemically reactive than secondary or tertiary amines. Therefore, essentially only the full-length oligonucleotides will form a covalent bond to the array surface. After deposition, the array substrate is processed to remove the non-bound material, such as the shorter-length oligonucleotides. The resulting array comprises features with a high concentration of full-length oligonucleotides bound to the array surface.

In another embodiment, a method of making oligonucleotide arrays from a mixture of oligonucleotides is provided, in which the mixture comprising full-length oligonucleotide and shorter-length oligonucleotide each having a 5'-end and a 3'-end. The method includes reacting a linking agent with the full-length oligonucleotide to couple a linking group to an end of the full-length oligonucleotide. The oligonucleotide mixture is deposited without separate purification, on a surface of the array for attachment to the surface, the linking group on the end of the full-length oligonucleotide preferentially attaching to the surface of the array over other groups present on the full-length and shorter length oligonucleotides of the mixture. Optionally, in any of the embodiments there may be at least 10% (by molar), or even at least 15% or 20% of the shorter length oligonucleotides present in the deposited mixture.

The method of the present invention advantageously adds a linking group only to the full-length oligonucleotides during the synthesis process. The linking group is the means for attachment of the full-length oligonucleotides to the array surface. After a procedure to cleave and deprotect the oligonucleotides, a high percentage of the full-length oligonucleotides having the linking group will attach to the array surface during the deposition step. The method of the present invention advantageously avoids the conventional purification step, while still achieving high fidelity full-length oligonucleotide features and saving in manufacturing time and cost.

BRIEF DESCRIPTION OF THE DRAWINGS

The various features and advantages of the present invention may be more readily understood with reference to the following detailed description taken in conjunction with the accompanying drawings, where like reference numerals designate like structural elements, and in which.

MODES FOR CARRYING OUT THE INVENTION

Definitions

Figure 1:
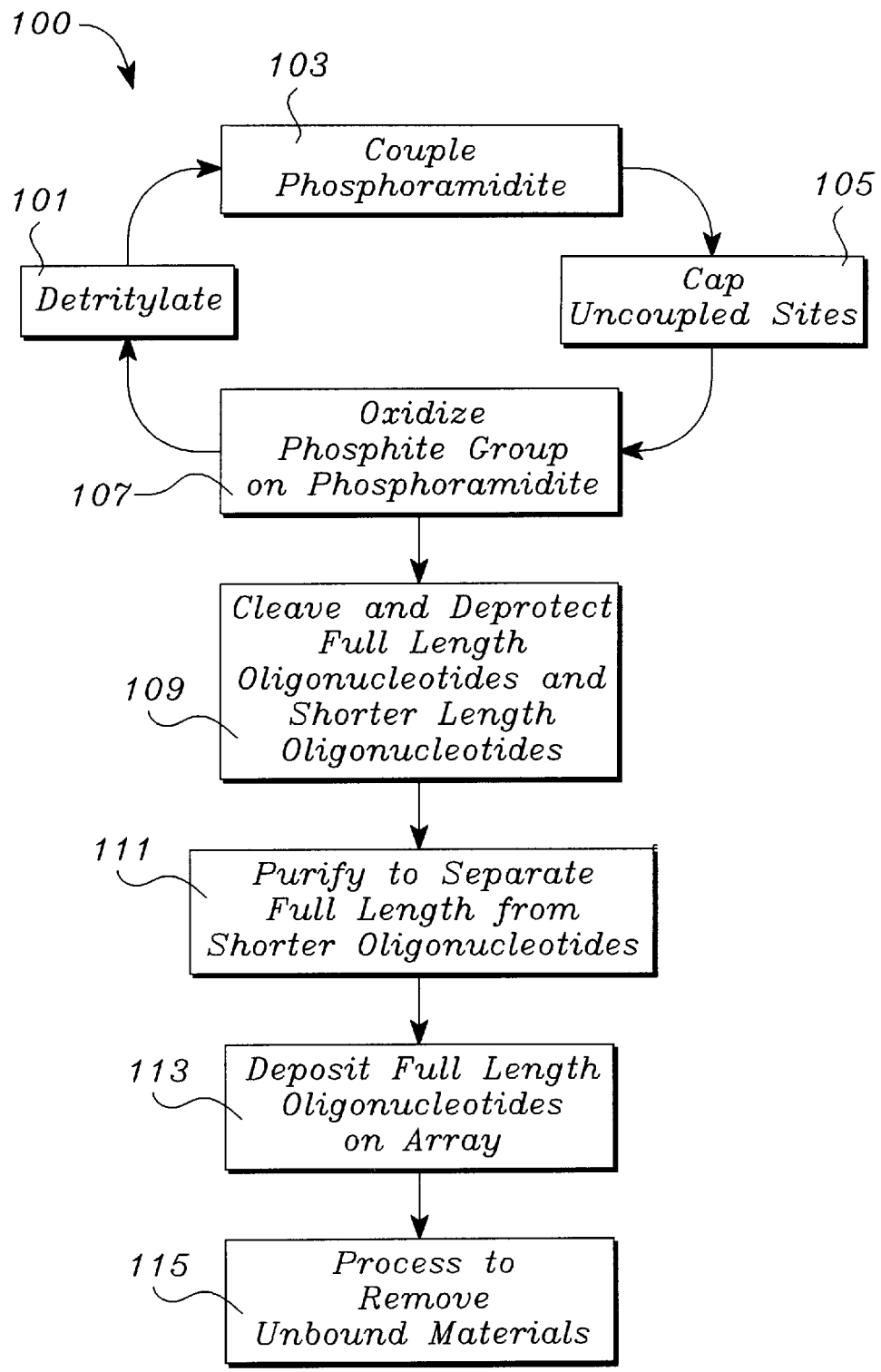
FIG. 1 is a block diagram that illustrates the conventional oligonucleotide array synthesis process.

The following terms are intended to have the following general meanings as they are used herein:

Polynucleotide—a compound or composition that is a polymeric nucleotide or nucleic acid polymer. The polynucleotide may be a natural compound or a synthetic compound. In the context of an assay, the polynucleotide can have from about 5 to 5,000,000 or more nucleotides. The larger polynucleotides are generally found in the natural state. In an isolated state the polynucleotide can have a bout 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA, double-stranded or single stranded (dsDNA and ssDNA), and RNA, including t-RNA, m-RNA, r-RNA, mitochondrial DNA and RNA, chloroplast DNA and RNA, DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like. Polynucleotide includes nucleic acid polymers having a modified backbone or modified nucleotide bases, such as protein-nucleic acids (PNAs) or PNA hybrids, as disclosed in U.S. Pat. No. 5,948,902.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, double stranded DNA (dsDNA) can be heated at 90–100° C. for a period of about 1 to 10 minutes to produce denatured material, while RNA produced via transcription from a dsDNA template is already single stranded. Further for the purposes the invention, the term "polynucleotide" is interchangeable with the term "oligonucleotide".

Oligonucleotide—a polynucleotide, usually single stranded, usually a synthetic polynucleotide but may be a naturally occurring polynucleotide. The oligonucleotide(s) are usually comprised of a sequence of at least 5 nucleotides, usually, 10 to 100 nucleotides, more usually, 20 to 50 nucleotides, preferably, 10 to 30 nucleotides, more preferably, 20 to 30 nucleotides, and desirably about 25 nucleotides in length. For the purposes of the invention, the terms oligonucleotide and polynucleotide are used interchangeably herein and shall have the meanings as defined herein, unless noted otherwise.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described in J. Messing (1983) Methods Enzymol. 101:20–78, incorporated herein by reference.

Other methods of oligonucleotide synthesis include phosphotriester and phosphodiester methods (Narang, et al., (1979) Meth. Enzymol 68:90) and synthesis on a support (Beaucage, et al. (1981) Tetrahedron Letters 22:1859–1862) as well as phosphoramidate techniques (Caruthers, M. H., et al., "Methods in Enzymology," Vol. 154, pp. 287–314 (1988) and others described in "Synthesis and Applications of DNA and RNA," S. A. Narang, editor, Academic Press, New York, 1987, and the references contained therein. Sequential addition of nucleotide phosphoramidites to surface-linked hydroxyl groups is described by T. Brown and Dorcas J. S. Brown in *Oligonucleotides and Analogues A Practical Approach*, F. Eckstein, editor, Oxford University Press, Oxford, pp 1–24 (1991). The chemical synthesis via a photolithographic method of spatially addressable arrays of oligonucleotides bound to glass surfaces is described by A. C. Pease, et al., Proc. Nat. Aca. Sci. USA (1994) 91:5022–5026. Attachment of pre-synthesized oligonucleotides may be accomplished by (1) covalent linkage of a chemically modified oligonucleotide (e.g. aliphatic 1° amine) to the substrate surface bearing an amine-reactive group (e.g. aromatic isothiocyanate) as described in Z. Guo, R. A. Guilfoyle, A. J. Thiel, R. Wang, L. M. Smith, *Nucleic Acids Res* 22, 5456–65 (1994), or (2) adsorption to a substrate surface coated with a positively charged polyelectrolyte (e.g. poly-L-lysine), followed by cross-linking to the surface chemically or photochemically (e.g. covalent stabilization via ultraviolet (UV) photo-crosslinking), as described in M. Schena, D. Shalon, R. W. Davis, P. O. Brown, *Science,* 270, 467–70 (1995). Common deposition equipment used for forming arrays includes that described in M. Schena et al. (cited above), A. C. Pease et al., *Proc. Natl. Acad. Sci. USA,* 91, 5022–6 (1994) and A. P. Blanchard, R. J. Kaiser, L. E. Hood, *Biosensors & Bioelectronics* 11, 687–690 (1996). All of the references cited above are incorporated herein by reference. Purification after synthesis can be performed using polyacrylamide gel electrophoresis (PAGE) or liquid chromatography, such as High Performance Liquid Chromatography (HPLC), which is best described in Wu, R. et al., (1984) "Purification and sequence analysis of synthetic oligodeoxyribonucleotides", *In Oligonucleotide Synthesis: a practical approach,* (Gait, M. J., Editor), IRL Press, Oxford, pp. 135–151.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Phosphoramidite—formula I covers phosphoramidites (also known as a "phosphite triester), phosphites and H-phosphonates. For the purposes of the invention, when used herein, the term "phosphoramidite(s)" includes the terms "phosphite(s)" and "H-phosphonate(s)", unless otherwise noted.

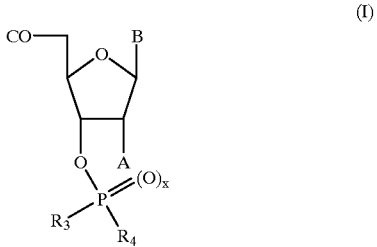

in which:

A represents H or an optionally protected hydroxyl group;

B is a purine or pyrimidine base whose exocyclic amine functional group is optionally protected; however, when B is replaced with A, formula I represents a phosphodiester or phosphotriester;

C is a conventional protective group for the 5'—OH functional group and does not have its conventional meaning for 'carbon', unless noted otherwise;

x=0 or 1 provided:

a) when x=1:

R$_3$ represents H and R$_4$ represents a negatively charged oxygen atom; or R$_3$ is an oxygen atom and R$_4$ represents either an oxygen atom or an oxygen atom carrying a protecting group; and b) when x=0:

R$_3$ is an oxygen atom carrying a protecting group and R$_4$ is either a hydrogen or a di-substituted amine group.

When x is equal to 1, R$_3$ is an oxygen atom and R$_4$ is an oxygen atom, the method is in this case the so-called phosphodiester method; when R$_4$ is an oxygen atom carrying a protecting group, the method is in this case the so-called phosphotriester method.

When x is equal to 1, R$_3$ is a hydrogen atom and R$_4$ is a negatively charged oxygen atom, the method is known as the H-phosphonate method.

When x is equal to 0, R$_3$ is an oxygen atom carrying a protecting group and R$_4$ is a halogen, the method is known as the phosphite method and, when R$_4$ is a leaving group of the di-substituted amine type, the method is known as the phosphoramidite method.

Nucleotide—the monomeric unit of nucleic acid polymers, i.e., DNA and RNA, which comprises a nitrogenous heterocyclic base, which is a derivative of either a purine or pyrimidine, a pentose sugar, and a phosphate (or phosphoric acid). When the phosphate is removed, the monomeric unit that remains is a "nucleoside". Thus a nucleotide is a 5'-phosphate of the corresponding nucleoside. When the nitrogenous base is removed from the nucleotide, the monomeric unit that remains is a "phosphodiester". A nucleotide is a phosphoramidite during synthesis of an oligonucleotide. For the purposes of the invention, the term "nucleotide" includes its corresponding phosphoramidite, nucleoside and phosphodiester, and "oligonucleotide" includes its corresponding oligonucleoside and oligophosphodiester, unless indicated otherwise. Other examples include abasic phosphodiesters, such as polyethers, and protein-nucleic acid (PNA) hybrids.

Modified nucleotide—a nucleotide that contains a modified base, sugar or phosph(ate) or (ite) group. The modified nucleotide can be produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth. For the purposes of the invention, modified nucleotide includes modified phosphoramidites.

Substrate or support—a porous or non-porous water insoluble material. The surface can have any one of a number of shapes, such as strip, plate, disk, rod, particle, including bead, and the like. The substrate can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. A commonly used support is Controlled Pore Glass (CPG), which consists of a glass matrix prepared uniformly with pores of defined size.

Immobilization of oligonucleotides on a substrate or surface may be accomplished by well-known techniques, commonly available in the literature. See, for example, A. C. Pease, et al., *Proc. Nat. Acad. Sci. USA,* 91:5022–5026 (1994), incorporated herein by reference.

DETAILED DESCRIPTION OF THE INVENTION

The present invention is a method of making oligonucleotide arrays having a high concentration of full-length oligonucleotides without the conventional step of purification. Advantageously, the present method provides for synthesizing the full-length oligonucleotides using conventional methods in a conventional DNA synthesizer, except that after the full-length oligonucleotides are synthesized, a linking agent is coupled to the full-length oligonucleotide before the oligonucleotides are cleaved from the DNA synthesizer support. The coupling of the linking agent to the full-length oligonucleotide replaces the need for the conventional purification step, as is further described below.

FIG. 1 illustrates a block diagram of one conventional oligonucleotide synthesis method using the phosphite-triester (or phosphoramidite) approach for array fabrication. Other oligonucleotide synthesis methods, including but not limited to the H-Phosphonate method and the phosphoramidite method of synthesizing oligoribonucleotides, are equally applicable to the discussion below.

A nucleoside is attached to a solid support, typically CPG, by a covalent reaction between the 3' hydroxyl group on the nucleoside and a linker to the support. The CPG may be purchased with a first nucleoside already attached thereto. An oligonucleotide is synthesized typically from the 3' to the 5' direction, although synthesis from the 5' end to the 3' end is also known. The discussion below will describe the conventional 3'→5' synthesis direction with reference to FIG. 1. However, it should be noted that the invention is applicable synthesis methods using either the 3'→5' or 5'→3' synthesis directions. The oligonucleotide chain is grown by nucleophilic attack of the 5' hydroxyl of the immobilized nucleoside on the support. At the start of the synthesis process, the 5' hydroxyl group on the support-linked nucleoside is temporarily protected by alkylation with 4',4'-dimethoxytritylchloride (DMT), for example. The protecting group must be removed to grow the oligonucleotide chain. Moreover, each phosphoramidite that is subsequently added to grow the chain comprises a 5' protecting group, such as DMT, which is removed to add another phosphoramidite.

Referring to FIG. 1, a 5'-DMT protected coupled phosphoramidite is detritylated (step 101) to ready the phosphoramidite for coupling to another phosphoramidite at its deprotected 5'-end. The DMT is cleaved from the 5'-end by conventional treatment with trichloroacetic acid (1–3% w/v) in dichloromethane in less than 1 minute, for example.

The deprotected coupled phosphoramidite is coupled (step 103) with another phosphoramidite that has been activated at its 3'-phosphoramidite function by treating it with a weak acid, such as tetrazole. The activated phosphoramidate comprises the next nitrogenous base to be added to the oligonucleotide chain. The activated phosphoramidite contains a DMT protected 5'-end and is coupled to the deprotected 5'-end of the previously coupled phosphoramidite via the activated phosphite group at its 3'-end.

Each coupling step 103 is not 100% efficient. Typically, each coupling step is about 97% to 99% efficient. So some small amount of the de-protected 5' sites do not couple with the next phosphoramidite during the coupling step. For example, for a coupling efficiency of 98% for a 20 nucleotide long oligonucleotide, the percentage of the correct full length oligonucleotide will be approximately 67% ($0.98^{20}$). In order to prevent incorrect sequences (called deletions), the shorter-length oligonucleotides are prevented from coupling to a phosphoramidite in a later coupling step. Therefore, the shorter length or "failed" oligonucleotides are capped (step 105) to block a later coupling reaction. The free hydroxyl groups on the 5' end of the failed oligonucleotides are capped by acetylation using a strong acetylation reagent, such as N-acetyldimethyl-aminopyridinium ion, which is formed from a reaction between acetic anhydride and 4-dimethylaminopyridine (DMAP) or N-methyl-imidazole. This or other acetylation methods may be used, which are well known in the art.

The synthesis solution now comprises a growing oligonucleotide chain and possibly some uncoupled shorter length oligonucleotides that have been capped to prevent future phosphoramidite addition. Each phosphoramidite added to the growing oligonucleotide chain has an unstable phosphite internucleotide linkage at its 3' end, so the phosphite linkage is oxidized or stabilized (step 107) to a stable pentavalent phosphate triester bond using iodine in basic tetrahydrofuran solution with water, for example. After the oxidation step 107, the growing oligonucleotide chains are ready for the addition of other phosphoramidites.

The steps 101–107 are repeated until the desired full-length oligonucleotide is synthesized. The phosphoramidites are added sequentially at the 5' hydroxyl site where the protecting group has been removed in the detritylation step 101.

After the full-length oligonucleotide is synthesized, it is cleaved from the support and its nitrogenous bases and phosphate group are simultaneously deprotected (step 109) by treatment with ammonium hydroxide and/or methylamine under well-known conditions.

As mentioned above, the synthesis of oligonucleotides according to the conventional methods result in "failed chains" that accumulate progressively as a function of the oligonucleotide chain length. Failed chains include truncated chains, such as prematurely terminated chains, base-modified chains, and failed chains resulting from chain cleavage during deprotection. There is no single source of such failed chain impurities, to which coupling efficiencies certainly contribute. Since the synthesis method 100 described above includes some failed chains, such as "shorter-length" oligonucleotide, with the full-length oligonucleotide, the shorter length oligonucleotide must be separated out of the solution, so that primarily only the full-length oligonucleotide is deposited onto the array surface to form the array of full-length oligonucleotide features. Separating out the failed chains or "purifying" the full-length oligonucleotide is a very important step to achieving high fidelity arrays. The solution is purified (step 111) using the well-known methods of solid phase chromatography, polyacrylamide gel electrophoresis or liquid chromatography.

The purified solution of full-length oligonucleotide is deposited (step 113) on the surface of the array using well known manual or automatic means of spotting the full-length oligonucleotide on the feature areas. The purified full-length oligonucleotides are linked to the array via conventional methods of attachment to a substrate.

The method 200 of making high fidelity full-length oligonucleotide arrays according to the present invention advantageously comprises steps 101 to 109, 113 and 115, as described above, for the conventional method 100, so that the same well-established equipment, materials and processes can be used. However, the method 200 of the invention, advantageously avoids the costly and time consuming purification step 111 while still achieving a high fidelity or purity full-length oligonucleotide array.

Figure 2:
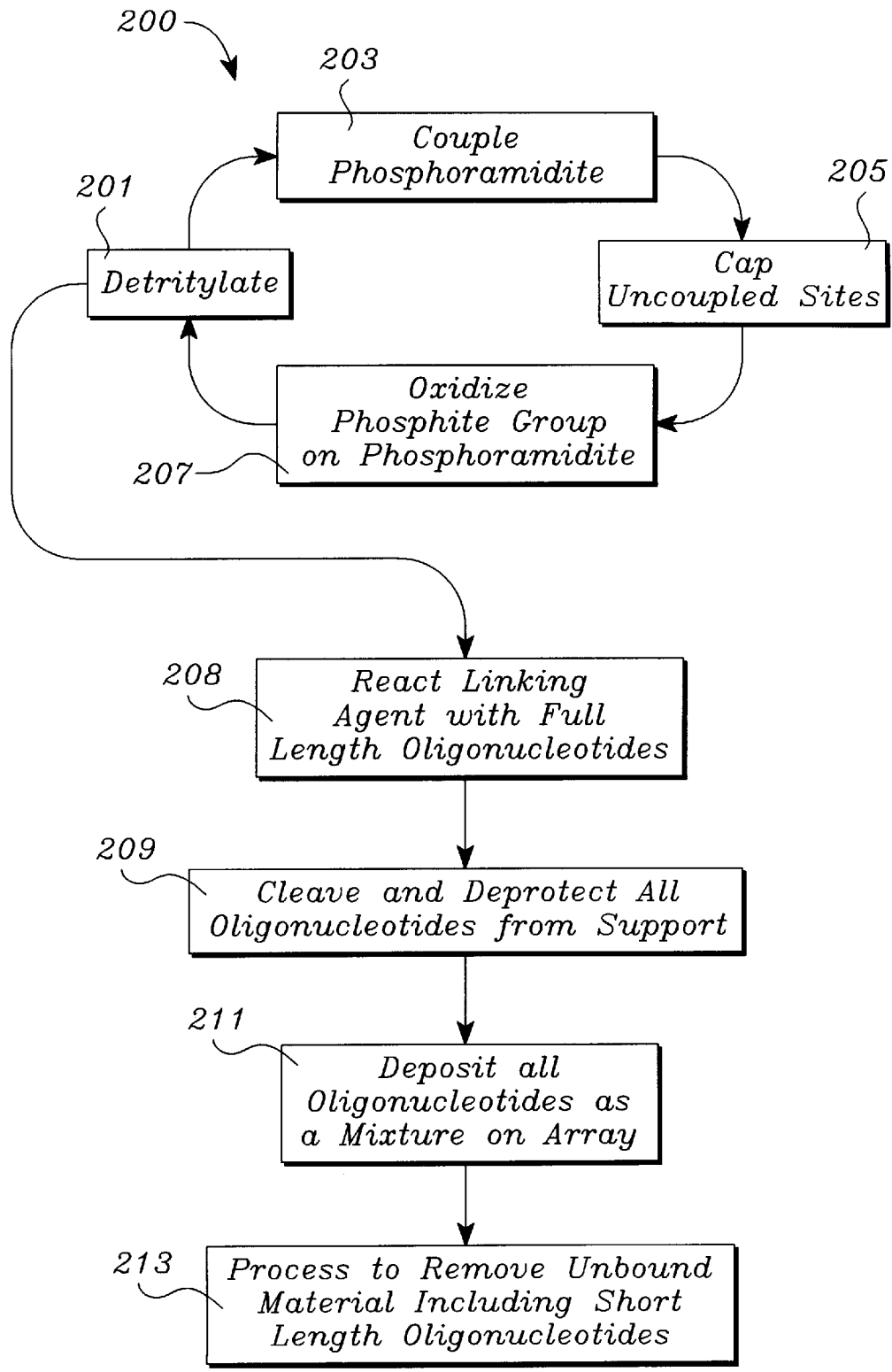
FIG. 2 is a block diagram that illustrates the method of the present invention.

FIG. 2 illustrates a block diagram of the method 200 of making full-length oligonucleotide arrays according to the invention. Steps 201–207, 209 and 213 in FIG. 2 are essentially the same as their conventional counterparts (101–109, 113 and 115) in FIG. 1. However, after the last step of oxidizing 207, when the desired length ("full-length") oligonucleotide has been synthesized, an additional detritylation step 201 is preformed to unblock the 5'-end of the full-length oligonucleotide. The unblocked full-length oligonucleotide is reacted (step 208) with a linking agent. The linking agent adds a linking group to the free-end of the full-length oligonucleotide, but not the shorter-length oligonucleotides because they are capped at their free-end in step 205.

The linking agent is an agent selected from an amine-providing agent, a carboxylic-providing agent or a thiol-providing agent, for example, that can form a covalent bond with an array substrate surface, but that does not react with any other group on the capped shorter-length oligonucleotides. Such linking agents are described by Rainer Bischoff et al., "Introduction of 5'-Terminal Functional Groups into Synthetic Oligonucleotides for Selective Immobilization", *Analytical Biochemistry,* 164, 336–344 (1987) and the references cited therein, all of which are incorporated herein by reference, for example. In the preferred embodiment, an amine providing agent is used, which is selected from amine-modified phosphoramidites, or other agents or reactants that add an amino group to the last nucleotide of the full-length oligonucleotide chain, but does not add an amino group to the capped shorter-length oligonucleotides. More preferably, the amine-modified phosphoramidites are used, and most preferably, the 5'-amine modified phosphoramidites are used. The amine modified phosphoramidite is coupled to the full-length oligonucleotide in the same fashion as the other phosphoramidites were coupled (step 203) to the growing oligonucleotide chain. When the 5'-amine modified phosphoramidite is used to coupled to the full-length oligonucleotide, an amino group replaces the conventional DMT protecting group on the 5'-end of the amine modified phosphoramidite. The preferred amino group on the 5'-end of the amine modified phosphoramidite is a trifluoroacetyl amino (TFA) group, although other amine-modified groups may be used on the modified phosphoramidite, such as MMT. The TFA group is preferred because it is base labile and thus advantageously reduced during the conventional cleave and deprotection step 209, as described below. The TFA group includes, but is not limited to, for example, a six carbon (C6) TFA, a three carbon (C3) TFA, among others. The C6 TFA is preferred because it provides more space between the 5'-amine moiety and the full-length oligonucleotide.

Figure 3:
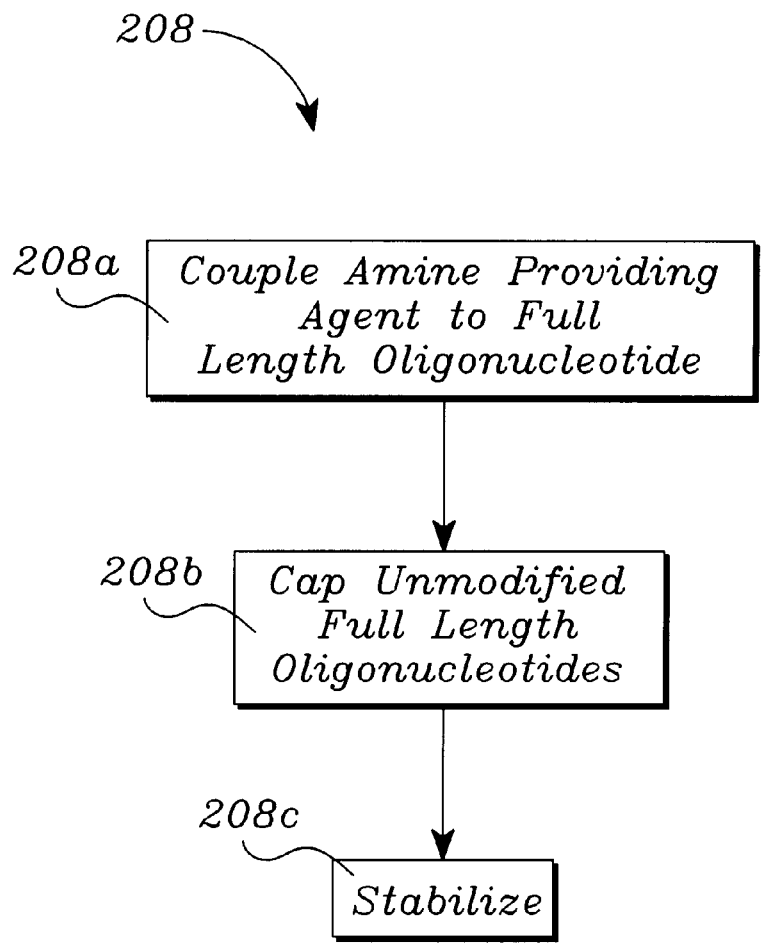
FIG. 3 is a block diagram that further illustrates step 208 of FIG. 2 in the preferred embodiment.

The step of reacting 208 is illustrated in FIG. 3 for the preferred embodiment The amine providing agent is coupled (step 208a) to the full-length oligonucleotide. The amine-providing agent adds an amino group to the deprotected 5'-end of the full-length oligonucleotides. Then capping step 208b is performed to cap any full-length oligonucleotide that did not successfully couple with the amine-providing agent. The capping process can be the same as used in the step 105, 205, described above. Then the linkage between the amine-providing agent and the full-length oligonucleotide is stabilized (step 208c). In the more preferred embodiment where the amine-providing agent is the amine modified phosphoramidite, the phosphite group on the modified full-length oligonucleotide is oxidized (step 208c) in the same way as step 107, 207, described above, to stabilize the phosphate triester bond between the full-length oligonucleotide and the amine-modified phosphoramidite.

The full-length oligonucleotide with a linking group attached thereto by the linking agent is hereinafter referred to as a "modified full-length oligonucleotide" of the invention. Referring back to FIG. 2, the oligonucleotides are cleaved from the support and deprotected (step 209), thereby producing a mixture of modified full-length oligonucleotides, capped full-length oligonucleotides and capped shorter-length oligonucleotides. In the preferred embodiment, the step of cleaving and deprotecting 209 also converts the amino group on all modified full-length oligonucleotides to a primary amine. For the invention, standard CPG supports are used, which do not comprise a linker that provides the same linking group as the linking agent upon cleavage from the support.

This mixture is deposited (step 211) onto an array substrate using conventional deposition equipment and methods, advantageously without first separating or purifying the mixture to separate out the desired full-length oligonucleotides. Quite advantageously, during the deposition process 211, the modified full-length oligonucleotides will preferentially attach to the substrate due to the higher chemical reactivity of the linking group on the free-end of the oligonucleotide over other groups contained within the structure or at a free-end of the oligonucleotides, including the shorter-length oligonucleotides. Thus, the modified full-length oligonucleotides will react faster and bond to the array surface before any capped full-length oligonucleotides in the mixture will bond, and in particular, before any of the shorter-length oligonucleotides in the mixture will bond, because neither of these oligonucleotides has higher reactivity linking group available for bonding. Therefore, the step of depositing 211 also functions as a purification step, which occurs simultaneously with the attachment of the oligonucleotides on the array. In the preferred embodiment, the higher reactivity linking group is the primary amine formed during the cleavage step 209. The primary amine has higher chemical reactivity than secondary or tertiary amines that may be included in the structure of the shorter-length oligonucleotides. It should be noted that some bonding of other groups, such as the secondary and tertiary amines, on the shorter-length oligonucleotides to the surface of the array may occur during the deposition step 211. The occurrence of this undesirable bonding introduces shorter length or incorrect sequence impurities ("impurities") into the array fabricated in accordance with the invention. Advantageously, the percentage of this impurity introduced is related to the preferential attachment ratio of the linking group to other groups available for bonding, and preferably, to the preferential attachment ratio of primary amines to secondary and tertiary amines, as described further below.

After deposition 211, and depending on the surface of the array used, the array substrates or slides are processed by either leaving them to dry overnight or rehydrating them in a humidified chamber overnight. Following the overnight drying or rehydration, the array slides are passivated with a mixture of reagents to deactivate or block non-specific binding sites on areas of the array slide surface not containing oligonucleotide features. In other instances, the array slides are subjected to various steps in order to stabilize the covalent bond between the oligonucleotide and the surface chemistry of the array slide surface, which are well-known in the art.

The array is processed (step 213) to remove the non-bound material, including the shorter-length oligonucleotides and to inactivate any chemically active sites remaining on the surface. The processing step preferably comprises washing the array with 6× SSPE and 0.005% Triton-X-100 for 1 minute; washing the array with 0.1× SSPE and 0.005% Triton X-100 at 37° C. for 15 minutes with stirring; and performing a final wash in 0.1× SSPE with no Triton X-100 at 4° C. for 2 minutes; followed by centrifuging the array slides at 1200 rpm for 1 min. to dry.

Thus, the present method 200 avoids the conventional separate purification step 111, which is expensive, time consuming, prone to loss of product and dilution of the final concentration of the oligonucleotide solution for deposition. The method 200 not only overcomes the disadvantages of the conventional methods, it does so while achieving a high fidelity or purity oligonucleotide array. High fidelity full-length oligonucleotide arrays are synthesized by the present method 200 with greater than 90% purity at a lower cost and faster turn around time than the full-length oligonucleotide arrays produced by conventional methods, such as method 100 described above.

In accordance with the method 200 of the invention, the preferential attachment ratio of the linking group over other groups that are free to attach improves the percentage of full-length oligonucleotides that attach to the array substrate. The result is a higher percentage of full-length oligonucleotides attached to the surface of the array, or alternatively, a lower percentage of shorter-length oligonucleotides attached to the array. For the invention, the preferential attachment ratio of the linking agent is as little as about 5:1 to achieve a high purity of greater than 90%, and preferably the preferential attachment ratio is from about 10:1 to about 30:1. Primary amines typically have a preferential attachment ratio as low as 5:1 and as high as 30:1 over secondary or tertiary amines to achieve >90% purity. By 90% purity, it is meant that the percentage of modified full-length oligonucleotide present on the array after step 213 is equal to or greater than 90%. Alternatively, a 90% purity means that the percentage of shorter-length oligonucleotides or impurities present on the array is equal to or less than 10%, in accordance with the method 200 of the invention.

As another example, consider a final mixture at step 209 that has 50% modified full length product with a primary amine and 50% shorter length or incorrect sequences without a primary amine. If there is a 10:1 preferential attachment ratio of the modified full length oligonucleotide, then only one in ten or 10% of the original 50% of the shorter or incorrect sequences or 5% (0.10×0.50) will also attach to the array surface. Thus, this example yields approximately 95% modified full-length oligonucleotides attached to the array surface, or a 95% purity, and an impurity of only 5%, in accordance with the invention.

The fabricated array according to the method 200 of the invention is used to evaluate polynucleotide or oligonucleotide "target" samples to be tested. A user will expose the array to a sample, such as in hybridizing or binding assays, and interrogate the array following such exposure using well-known conventional methods. The interrogation will produce a result. Information about the target sample can be obtained from the results of the interrogation. The user may be in a location remote to the location where the array is fabricated. The user may communicate the results or the information obtained from the results to a location remote to the user's location. A location is remote if it is at least a different location, e.g., a different building, a different city, different state or different country.

Thus there has been described a new method of making high fidelity full-length oligonucleotide probe arrays that avoids the conventional separate purification step and its inherent problems, yet still yields high fidelity arrays at a lower cost and faster turn-around time. It should be understood that the above-described embodiments are merely illustrative of some of the many specific embodiments that represent the principles of the present invention. Clearly, numerous other arrangements can be readily devised by those skilled in the art without departing from the scope of the present invention.

What is claimed is:

1. A method of making a full length oligonucleotide array from a mixture of pre-synthesized oligonucleotides on a support, the mixture comprising full-length oligonucleotide and shorter-length oligonucleotide each having a 5'-end and a 3'-end, a free-end of the full-length oligonucleotide having a protecting group and a free-end of the shorter-length oligonucleotide having a capping group, the other-end of each oligonucleotide being the linked end that is attached to the support, the method comprising the steps of:

reacting a linking agent with the full-length oligonucleotide to couple a linking group to the free-end of the full-length oligonucleotide;

cleaving the other-end of the oligonucleotides in the mixture from the support; and depositing without separately purifying the oligonucleotide mixture on a surface of an array substrate for attachment to the surface, the linking group on the free-end of the full-length oligonucleotide preferentially attaching to the surface of the substrate over other groups present on the full-length and shorter length oligonucleotides of the mixture thereby forming the full length oligonucleotide array.

2. The method of claim 1, further comprising the step of processing the array of deposited oligonucleotide to remove unattached materials including the capped shorter-length oligonucleotide.

3. The method of claim 1, wherein the step of reacting a linking agent comprises the steps of:

deprotecting the free-end of the full-length oligonucleotide by removing the protecting group; and coupling the linking group to the deprotected free-end of the full-length oligonucleotide; and capping the free-end of any uncoupled deprotected full-length oligonucleotide.

4. The method of claim 1, wherein the linking agent is selected from amine-providing agents, carboxylic-providing agents or thiol-providing agents, that do not react with any other groups in the mixture of oligonucleotides.

5. The method of claim 4, wherein the linking agent is an amine-providing agent selected from amine-modified phosphoramidites.

6. The method of claim 5, wherein the step of cleaving simultaneously converts an amino group on the free-end of the full-length oligonucleotide to a primary amine that is more reactive than secondary or tertiary amines in the mixture of oligonucleotides.

7. The method of claim 1, additionally comprises washing the array to remove unattached materials including the capped shorter-length oligonucleotide.

8. The method of claim 1, wherein the step of cleaving comprises the step of simultaneous deprotecting nitrogenous bases and phosphate groups on the pre-synthesized oligonucleotides in the mixture.

9. The method of claim 1, wherein the full-length oligonucleotide array comprises equal to or greater than 90% full-length oligonucleotide.

10. The method of claim 1, wherein the linking group has a preferential attachment ratio to the substrate surface of at least about 5:1 over other groups in the oligonucleotide mixture.

11. The method of claim 1, wherein the linking group has a preferential attachment ratio to the substrate surface of from about 10:1 to 30:1 over other groups in the oligonucleotide mixture.

12. The method of claim 5, wherein the primary amine has a preferential attachment ratio to the substrate surface of at least 5:1 over secondary amines and tertiary amines.

13. The method of claim 12, wherein the primary amine has a preferential attachment ratio to the substrate surface of from about 10:1 to about 30:1 over secondary amines and tertiary amines.

14. The method of claim 5, wherein the amine-modified phosphoramidite comprises a 5'-end and a 3'-end, one of the ends comprising an amino group that is converted to a primary amine during the step of cleaving, the other of the ends comprising a phosphite group that links to the deprotected free-end of the full-length oligonucleotide during the step of reacting.

15. The method of claim 14, wherein the step of reacting further comprises the step of stabilizing the phosphite group on the other-end of the amine-modified phosphoramidite by oxidizing the phosphite group to a phosphate group.

16. The method of claim 14, wherein the amino group on the amine-modified phosphoramidite comprises trifluoroacetylamino (TFA).

17. The method of claim 1, wherein the free-end of the full-length oligonucleotide and the free-end of the shorter-length oligonucleotide is the 5'-end and the other end is the 3'-end.

18. The method of claim 1, wherein the free-end of the full-length oligonucleotide and the free-end of the shorter-length oligonucleotide is the 3'-end and the other end is the 5'-end.

19. A method of making a full length oligonucleotide array from a mixture of pre-synthesized oligonucleotides on a support, the mixture comprising full-length oligonucleotide and shorter-length oligonucleotide each having a 5'-end and a 3'-end, one of the 5'- or 3'-ends being a free-end, the free-end of the full-length oligonucleotide having a protecting group and the free-end of the shorter-length oligonucleotide having a capping group, the other end of each oligonucleotide being the linked-end that is attached to the support, the method comprising the steps of:
 reacting an amine-providing agent with the full-length oligonucleotide to provide an amino group on the free-end of the full-length oligonucleotide;
 cleaving the linked-end of the oligonucleotides in the mixture from the support and simultaneously converting the amino group of the full-length oligonucleotide to a primary amine; and
 depositing without separately purifying the oligonucleotide mixture on a surface of an array substrate for attachment to the surface, the primary amine on the free-end of the full-length oligonucleotide preferentially attaching to the surface of the substrate over secondary or tertiary amines present on the full-length and shorter length oligonucleotides of the mixture, thereby forming the full length oligonucleotide array.

20. The method of claim 19, further comprising the step of processing the array of deposited oligonucleotides to remove unattached materials including the capped shorter-length oligonucleotide.

21. The method of claim 19, wherein the step of reacting comprises the steps of:
 deprotecting the free-end of the full-length oligonucleotide by removing the protecting group; and
 coupling the amine-providing agent to the deprotected free-end of the full-length oligonucleotide; and
 capping the free-end of any uncoupled deprotected full-length oligonucleotide.

22. The method of claim 19, additionally comprises washing the array to remove unattached materials including the capped shorter-length oligonucleotide.

23. The method of claim 19, wherein the step of cleaving comprises the step of simultaneous deprotecting nitrogenous bases and phosphate groups on the pre-synthesized oligonucleotides in the mixture.

24. The method of claim 19, wherein the oligonucleotide array comprises equal to or greater than about 90% full-length oligonucleotide.

25. The method of claim 19, wherein the oligonucleotide array comprises less than or equal to about 10% attached shorter-length oligonucleotides or other impurities.

26. The method of claim 19, wherein the primary amine has a preferential attachment ratio to the substrate surface of at least about 5:1 over secondary amines and tertiary amines.

27. The method of claim 19, wherein the primary amine has a preferential attachment ratio to the substrate surface of from about 10:1 to 30:1 over secondary amines and tertiary amines.

28. The method of claim 19, wherein the amine providing agent is selected from amine-modified phosphoramidites.

29. The method of claim 28, wherein the amine-modified phosphoramidite comprises a 5'-end and a 3'-end, one of the 3'- or 5'-ends comprising the amino group that is converted to a primary amine during the step of cleaving, the other of the 3'- or 5'-ends comprising a phosphite group that links to the deprotected free-end of the full-length oligonucleotide during the step of reacting.

30. The method of claim 29, wherein the step of reacting further comprises the step of stabilizing the phosphite group on the other-end of the amine-modified phosphoramidite linking to the full-length oligonucleotide by oxidizing the phosphite group to a phosphate group.

31. The method of claim 30, wherein the amino group on the amine-modified phosphoramidite comprises trifluoroacetylamino (TFA).

32. The method of claim 19, wherein the free-end of the full-length oligonucleotide and the free-end of the shorter-length oligonucleotide is the 5'-end and the other end is the 3'-end.

33. The method of claim 19, wherein the free-end of the full-length oligonucleotide and the free-end of the shorter-length oligonucleotide is the 3'-end and the other end is the 5'-end.

34. A method of making a full length oligonucleotide array having equal to or greater than 90% full-length oligonucleotides from a mixture of pre-synthesized oligonucleotides on a support, the mixture comprising full-length oligonucleotide and shorter-length oligonucleotide each having a 5'-end and a 3'-end, the 5'-end of the full-length oligonucleotide having a protecting group and the 5'-end of the shorter-length oligonucleotide having a capping group, the 3'-end of each oligonucleotide being the linked end that is attached to the support, the method comprising the steps of:
 reacting an amine-providing agent with the full-length oligonucleotide to provide an amino group on the 5'-end of the full-length oligonucleotide;
 cleaving the 3'-end of the oligonucleotides in the mixture from the support and simultaneously converting the amino group of the full-length oligonucleotide to a primary amine;
 depositing without separately purifying the oligonucleotide mixture on a surface of an array substrate for attachment to the surface, the primary amine on the 5'-end of the full-length oligonucleotide preferentially attaching to the surface of the substrate over secondary or tertiary amines present on the full-length and shorter length oligonucleotides of the mixture; and
 processing the array of deposited oligonucleotides to remove unattached materials including the capped shorter-length oligonucleotide, thereby forming the full length oligonucleotide tray.

35. A method of making a full length oligonucleotide array from a mixture of oligonucleotides, the mixture comprising full-length oligonucleotide and shorter-length oligonucleotide each having a 5'-end and a 3'-end, the method comprising the steps of:
 reacting a linking agent with the full-length oligonucleotide to couple a linking group to an end of the full-length oligonucleotide; and depositing without separately purifying the oligonucleotide mixture on a surface of an array substrate for attachment to the surface, the linking group on the end of the full-length oligonucleotide preferentially attaching to the surface of the substrate over other groups present on the full-length and shorter length oligonucleotides of the mixture, thereby forming the full length oligonucleotide array.

36. A method according to claim 35 wherein one end of the full-length oligonucleotide has a protecting group and an end of the shorter-length oligonucleotide has a capping group, the method additionally comprising deprotecting the one end of the full-length oligonucleotide by removing the protecting group prior to coupling with the linking agent.

37. A method according to claim 1 wherein at least 10% by molar, of the shorter length oligonucleotides is present in the deposited mixture.

38. A method according to claim 19 wherein at least 10% by molar, of the shorter length oligonucleotides is present in the deposited mixture.

39. A method according to claim 35 wherein at least 10% by molar, of the shorter length oligonucleotides is present in the deposited mixture.

40. A method according to claim 1 wherein at least 15% by molar, of the shorter length oligonucleotides is present in the deposited mixture.

41. A method according to claim 1 wherein at least 20% by molar, of the shorter length oligonucleotides is present in the deposited mixture.

42. A method according to claim 19 wherein at least 20% by molar, of the shorter length oligonucleotides is present in the deposited mixture.

* * * * *